(12) United States Patent
Bentley et al.

(10) Patent No.: US 7,872,072 B2
(45) Date of Patent: Jan. 18, 2011

(54) BRANCHED POLYMERS AND THEIR CONJUGATES

(75) Inventors: Michael David Bentley, Huntsville, AL (US); Xuan Zhao, Huntsville, AL (US); Xiaoming Shen, Madison, AL (US); William Dudley Battle, III, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 275 days.

(21) Appl. No.: 11/336,695

(22) Filed: Jan. 20, 2006

(65) Prior Publication Data

US 2006/0178475 A1    Aug. 10, 2006

Related U.S. Application Data

(62) Division of application No. 10/290,082, filed on Nov. 7, 2002, now Pat. No. 7,026,440.

(60) Provisional application No. 60/337,613, filed on Nov. 7, 2001.

(51) Int. Cl.
 C08G 63/91 (2006.01)
 C08G 63/48 (2006.01)
 C07C 215/02 (2006.01)
(52) U.S. Cl. ............ 525/54.1; 525/54.2; 564/506; 568/62
(58) Field of Classification Search .............. 525/54.1, 525/54.11; 564/506; 568/62; 530/402, 409, 530/41
See application file for complete search history.

(56) References Cited

U.S. PATENT DOCUMENTS

| | | | |
|---|---|---|---|
| 5,122,614 A | 6/1992 | Zalipsky | |
| 5,605,976 A | 2/1997 | Martinez et al. | |
| 5,643,575 A * | 7/1997 | Martinez et al. | 424/194.1 |
| 5,681,567 A | 10/1997 | Martinez et al. | |
| 5,681,811 A | 10/1997 | Ekwuribe | |
| 5,684,096 A | 11/1997 | Taylor et al. | |
| 5,746,814 A | 5/1998 | Malhotra et al. | |
| 5,756,593 A | 5/1998 | Martinez et al. | |
| 5,874,500 A | 2/1999 | Rhee et al. | |
| 5,919,455 A | 7/1999 | Greenwald et al. | |
| 5,932,462 A | 8/1999 | Harris et al. | |
| 6,113,906 A | 9/2000 | Greenwald et al. | |
| 6,180,287 B1 | 1/2001 | Watanabe et al. | |
| 6,191,105 B1 * | 2/2001 | Ekwuribe et al. | 514/3 |
| 6,258,351 B1 | 7/2001 | Harris | |
| 6,348,558 B1 | 2/2002 | Harris et al. | |
| 6,362,254 B2 | 3/2002 | Harris et al. | |
| 6,497,895 B2 | 12/2002 | Uhrich | |
| 6,541,543 B2 * | 4/2003 | Harris et al. | 523/406 |
| 2002/0052443 A1 | 5/2002 | Greenwald et al. | |

FOREIGN PATENT DOCUMENTS

| | | |
|---|---|---|
| EP | 0899310 | 3/1999 |
| JP | 3067541 | 7/2000 |
| WO | 94/26778 | 11/1994 |
| WO | WO 94/26778 * | 11/1994 |
| WO | 9511924 A1 | 5/1995 |
| WO | 9841562 A1 | 9/1998 |
| WO | 01/49268 A1 | 7/2001 |
| WO | 02/060978 A1 | 8/2002 |
| WO | 03004021 T A3 | 5/2003 |

OTHER PUBLICATIONS

Choi, et al., "Star-Shaped Poly(ether-ester) Block Copolymers: Synthesis Characterization, and Their Physical Properties", *Macromolecules*, vol. 31, No. 25, pp. 8766-8774 (1998).
Schmalengerg, et al., "Cytotoxicity of a Unimolecular Polymeric Micelle and Its Degradation Products", *Biomacromolecules*, pp. A-E (2001).
Shearwater Polymers, Inc., Product Listing, pp. 1-49 (Catalog 1995).
Shearwater Polymers, Inc., Polyethylene Glycol Derivatives, pp. 1-53 (Catalog 1997-1998).
Shearwater Polymers, Inc., Polyethylene Glycol Derivatives, pp. 1-50 (Catalog 2000).
Shearwater Polymers, Inc., Polyethylene Glycol Derivatives for Biomedical Applications, pp. 1-17 (Catalog 2001).
International Search Report, corresponding to International Application No. PCT/US02/35759, mailed on May 16, 2003.
Written Opinion of the International Searching Authority, corresponding to International Application No. PCT/US02/35759, mailed on Jun. 24, 2003.
International Preliminary Examination Report, corresponding to International Application No. PCT/US02/35759, mailed on Sep. 19, 2003.
Notice of Grounds for Rejection issued Jun. 23, 2009, corresponding to Korean Patent Appl'n. No. 2004-7006961.
Notice of Reasons for Rejection mailed May 8, 2009, corresponding to Japanese Patent Appl'n. No. 2003-542253.

(Continued)

*Primary Examiner*—Shaojia Anna Jiang
*Assistant Examiner*—Ganapathy Krishnan
(74) *Attorney, Agent, or Firm*—Mark A. Wilson

(57) ABSTRACT

The present invention is directed to branched reactive water-soluble polymers comprising at least two polymer arms, such as poly(ethylene glycol), attached to a central aliphatic hydrocarbon core molecule through heteroatom linkages. The branched polymers bear at least one functional group for reacting with a biologically active agent to form a biologically active conjugate. The functional group of the branched polymer can be directly attached to the aliphatic hydrocarbon core or via an intervening linkage, such as a heteroatom, -alkylene-, —O-alkylene-O—, -alkylene-O-alkylene-, -aryl-O—, —O-aryl-, (—O-alkylene-)$_m$, or (-alkylene-O—)$_m$ linkage, wherein m is 1-10.

6 Claims, No Drawings

OTHER PUBLICATIONS

Notice of Reasons for Rejection mailed Aug. 1, 2008, corresponding to Japanese Patent Appl'n. No. 2003-542253.

Examiner's Report No. 2 dated Jun. 14, 2007, corresponding to Australian Patent Appl'n. No. 2002352524.

Requisition by the Examiner dated Sep. 8, 2009, corresponding to Canadian Patent Appl'n. No. 2,466,027.

Invitation to Pay Additional Fees and Communication Relating to the Results of the Partial International Search, mailed Mar. 5, 2003, corresponding to PCT Appl'n. No. PCT/US2002/35759.

* cited by examiner ated Nov. 7, 2002, issued as U.S. Pat.

BRANCHED POLYMERS AND THEIR CONJUGATES

CROSS-REFERENCE TO RELATED APPLICATIONS

This application is a divisional of U.S. patent application Ser. No. 10/290,082, filed Nov. 7, 2002, issued as U.S. Pat. No. 7,026,440, which claims the benefit of priority of Provisional Application Ser. No. 60/337,613, filed Nov. 7, 2001, which is incorporated herein by reference in its entirety.

FIELD OF THE INVENTION

This invention relates to branched, reactive water soluble polymers useful for conjugating to biologically active molecules and to methods for making and utilizing such polymers.

BACKGROUND OF THE INVENTION

Covalent attachment of the hydrophilic polymer poly(ethylene glycol), abbreviated PEG, is a highly advantageous method of increasing water solubility and bioavailability and extending the circulation time of many biologically active molecules, particularly hydrophobic molecules. For example, it has been shown that the water-insoluble drug, paclitaxel, when coupled to PEG, becomes water-soluble. Greenwald, et al., *J. Org. Chem.*, 60:331-336 (1995). The total molecular weight of the polymer or polymers attached to the biologically active molecule must be sufficiently high to impart the advantageous characteristics typically associated with PEG polymer attachment, such as increased water solubility and circulating half life, while not adversely impacting the bioactivity of the parent molecule.

Proteins and other molecules often have a limited number of reactive sites available for polymer attachment. Often, the sites most suitable for modification via polymer attachment play a significant role in receptor binding, and are necessary for retention of the biological activity of the molecule. As a result, indiscriminate attachment of polymer chains to such reactive sites on a biologically active molecule often leads to a significant reduction or even total loss of biological activity of the polymer-modified molecule. To form conjugates having sufficient polymer molecular weight for imparting the desired advantages to a target molecule, prior art approaches have typically involved either (i) random attachment of numerous polymer arms to the molecule, thereby increasing the risk of a reduction or even total loss in bioactivity of the parent molecule, or (ii) attachment of one or two very long polymer chains. Unfortunately, the use of very high molecular weight linear polymer chains is problematic because of the difficulty and expense associated with their preparation, purification, and associated instability.

Branched polymers comprising a plurality of polymer arms attached to a central core and having a single reactive group for conjugation to a biologically active molecule have been described in U.S. Pat. Nos. 5,643,575 and 5,932,462. Both patents describe branched polymers formed by covalent attachment of a water-soluble polymer such as an end-capped PEG to a central core molecule bearing amino groups, such as lysine or 1,3-diamino-2-propanol. Although these branched polymers are useful for attaching a high molecular weight polymer to a molecule at a single attachment site without using an extremely long polymer chain, the methods of forming the branched PEG molecules of the prior art is difficult and requires extensive purification of the PEG polymers prior to attachment to the core molecule and also purification/removal of partially pegylated polymer intermediates.

There remains a need in the art for new branched polymer reagents that provide the benefits associated with branched polymers (i.e., high overall molecular weight in a single non-linear polymer molecule), but are easier to synthesize or provide more flexibility in their design than prior art reagents.

SUMMARY OF THE INVENTION

The present invention is based upon the development of branched, reactive water-soluble polymers useful for conjugation to biologically active molecules in a manner that tends to avoid a significant reduction in the biological activity of the molecule while still providing the benefits of water-soluble polymer conjugation. The branched polymers of the invention can be readily synthesized from a number of aliphatic core structures that do not require the presence of activating groups suitable for coupling to an activated linear polymer, such as succinimidyl carbonate end-capped poly(ethylene glycol) or the like, for building the branched water soluble polymer. That is to say, the preparation of the polymers of the invention is not hampered by the need to utilize core structures having reactive functional groups necessary for coupling with the polymer arms, since the polymer portions of the molecule are generally built directly onto the core by polymerization of suitable monomer units.

In one aspect, the present invention provides a branched, reactive water-soluble polymer comprising at least two polymer arms, such as poly(ethylene glycol), attached to a central core molecule through heteroatom linkages such as ether linkages. The central core molecule is an aliphatic hydrocarbon having a length of at least three carbon atoms. The branched polymers of the invention are preferably although not necessarily monofunctional (i.e., having one reactive functional group suitable for covalent attachment to a biologically active agent), and the single functional group is preferably attached, optionally via an intervening linkage, to the aliphatic hydrocarbon core molecule.

Suitable polymers for use in preparing the branched polymer structures of the invention include poly(alkylene glycols), poly(oxyethylated polyol), poly(olefinic alcohol), poly (vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), poly(acrylic acid), carboxymethyl cellulose, hyaluronic acid, hydroxypropylmethyl cellulose, and copolymers, terpolymers, and mixtures thereof. In one embodiment of the invention, the polymer is a poly(ethylene glycol).

In another aspect, the invention provides a biologically active conjugate comprising a biologically active molecule, such as a protein, covalently attached to a branched polymer as described above. The biologically active molecule is preferably attached to the branched polymer via a linkage formed by reaction of a reactive functional group on the branched polymer with a suitable functional group on the biologically active molecule.

In yet another aspect, the invention provides a method of preparing branched reactive polymers comprising poly(alkylene glycol) polymer arms. The method includes polymerization of alkylene oxide monomer units, such as ethylene oxide, onto an aliphatic hydrocarbon core structure bearing at least two nucleophilic groups (e.g., thiol, amino or hydroxyl groups). Preferably, the nucleophilic groups are identical such as in propane substituted with hydroxyl groups at the 1- and 3-positions (1,3-propanediol) to, for example, favor polymerization rates that are comparable in each of the polymer arms. At least one reactive group suitable for further modification, typically in protected form such as a protected hydroxyl group, is also attached to the aliphatic hydrocarbon core, optionally via an intervening linkage. Following polymerization of the alkylene oxide monomer units onto the core molecule, and optional end-capping of the poly(alkylene glycol) polymer arms, the protecting group of the protected hydroxyl or other functional group is removed to provide a reactive group suitable for further modification, e.g., to form a branched polymer suitable for direct covalent attachment to a biologically active molecule to form a branched polymer conjugate.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

I. DEFINITIONS

The following terms as used herein have the meanings indicated.

As used in the specification, and in the appended claims, the singular forms "a", "an", "the", include plural referents unless the context clearly dictates otherwise.

The terms "functional group", "active moiety", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules. The term "active," when used in conjunction with a functional group, is intended to include those functional groups that react readily with electrophilic or nucleophilic groups on other molecules, in contrast to those groups that require strong catalysts or highly impractical reaction conditions in order to react (i.e., "non-reactive" or "inert" groups). For example, as would be understood in the art, the term "active ester" would include those esters that react readily with nucleophilic groups such as amines. Exemplary active esters include N-hydroxysuccinimidyl esters or 1-benzotriazolyl esters. Typically, an active ester will react with an amine in aqueous medium in a matter of minutes, whereas certain esters, such as methyl or ethyl esters, require a strong catalyst in order to react with a nucleophilic group. As used herein, the term "functional group" includes protected functional groups.

The term "protected functional group" or "protecting group" or "protective group" refers to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene, T. W., et al., *PROTECTIVE GROUPS IN ORGANIC SYNTHESIS*, 3rd ed., John Wiley & Sons, New York, N.Y. (1999).

The term "linkage" or "linker" (L) is used herein to refer to an atom or a collection of atoms used to link, preferably by one or more covalent bonds, interconnecting moieties such as two polymer segments or a terminus of a polymer and a reactive functional group present on a bioactive agent. A linker of the invention may be hydrolytically stable or may include a physiologically hydrolyzable or enzymatically degradable linkage.

A "physiologically hydrolyzable" or "hydrolytically degradable" bond is a weak bond that reacts with water (i.e., is hydrolyzed) under physiological conditions. Preferred are bonds that have a hydrolysis half life at pH 8, 25° C. of less than about 30 minutes. The tendency of a bond to hydrolyze in water will depend not only on the general type of linkage connecting two central atoms but also on the substituents attached to these central atoms. Appropriate hydrolytically unstable or degradable linkages include but are not limited to carboxylate ester, phosphate ester, anhydrides, acetals, ketals, acyloxyalkyl ether, imines, orthoesters, peptides and oligonucleotides.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

An "enzymatically unstable" or degradable linkage is a linkage that can be degraded by one or more enzymes.

The term "polymer backbone" refers to the covalently bonded chain of repeating monomer units that form the polymer. The terms polymer and polymer backbone are used herein interchangeably. For example, the polymer backbone of PEG is $-CH_2CH_2O-(CH_2CH_2O)_n-CH_2CH_2$ where n typically ranges from about 2 to about 4000. As would be understood, the polymer backbone may be covalently attached to terminal functional groups or pendant functionalized side chains spaced along the polymer backbone.

The term "reactive polymer" refers to a polymer bearing at least one reactive functional group.

Unless otherwise noted, molecular weight is expressed herein as number average molecular weight ($M_n$), which is defined as $$\frac{\sum NiMi}{\sum Ni},$$

wherein Ni is the number of polymer molecules (or the number of moles of those molecules) having molecular weight Mi.

The term "alkyl", "alkenyl", "alkynyl" and "alkylene" refers to hydrocarbon chains typically ranging from about 1 to about 12 carbon atoms in length, preferably 1 to about 6 atoms, and includes straight and branched chains. Unless otherwise noted, the preferred embodiment of any alkyl or alkylene referred to herein is C1-C6alkyl (e.g., methyl or ethyl).

"Cycloalkyl" refers to a saturated or unsaturated cyclic hydrocarbon chain, including bridged, fused, or spiro cyclic compounds, preferably comprising 3 to about 12 carbon atoms, more preferably 3 to about 8.

"Aryl" means one or more aromatic rings, each of 5 or 6 core carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

"Heteroaryl" is an aryl group containing from one to four heteroatoms, preferably N, O, or S, or a combination thereof, which heteroaryl group is optionally substituted at carbon or nitrogen atom(s) with C1-6 alkyl, —$CF_3$, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5-membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heteroaryls with three heteroatoms (e.g., 1,3,5-triazine); and 6-membered heteroaryls with four heteroatoms.

"Heterocycle" or "heterocyclic" means one or more rings of 5-12 atoms, preferably 5-7 atoms, with or without unsaturation or aromatic character and at least one ring atom which is not carbon. Preferred heteroatoms include sulfur, oxygen, and nitrogen. Multiple rings may be fused, as in quinoline or benzofuran.

"Heteroatom" means any non-carbon atom in a hydrocarbon analog compound. Examples include oxygen, sulfur, nitrogen, phosphorus, arsenic, silicon, selenium, tellurium, tin, and boron.

The term "drug", "biologically active molecule", "biologically active moiety" or "biologically active agent", when used herein means any substance which can affect any physical or biochemical properties of a biological organism, including but not limited to viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, polynucleotides, nucleic acids, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

"Polyolefinic alcohol" refers to a polymer comprising a polyolefin backbone, such as polyethylene, having multiple pendant hydroxyl groups attached to the polymer backbone. An exemplary polyolefinic alcohol is polyvinyl alcohol.

As used herein, "non-peptidic" refers to a polymer backbone substantially free of peptide linkages. However, the polymer backbone may include a minor number of peptide linkages spaced along the length of the backbone, such as, for example, no more than about 1 peptide linkage per about 50 monomer units.

By "residue" is meant the portion of a molecule remaining after reaction with one or more molecules. For example, a biologically active molecule residue in a branched polymer conjugate of the invention is the portion of a biologically active molecule remaining following covalent linkage to a branched polymer of the invention.

"Oligomer" refers to short monomer chains comprising 2 to about 10 monomer units, preferably 2 to about 5 monomer units.

The term "conjugate" is intended to refer to the entity formed as a result of covalent attachment of a molecule, e.g., a biologically active molecule, to a reactive polymer molecule, preferably a branched reactive polymer of the invention.

"Monofunctional" in the context of a polymer of the invention refers to a polymer possessing a single reactive functional group.

"Bifunctional" in the context of a polymer of the invention refers to a polymer possessing two reactive functional groups which may be the same or different.

"Multifunctional" in the context of a polymer of the invention means a polymer having 3 or more functional groups attached thereto, where the functional groups may be the same or different. Multifunctional polymers of the invention will typically comprise from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups attached to the polymer backbone.

II. BRANCHED REACTIVE POLYMERS

In one aspect, the present invention provides branched reactive polymers comprising at least two polymer arms, such as PEG arms, attached to a central core through heteroatom linkages such as ether linkages. The central core molecule is an aliphatic hydrocarbon having a carbon chain length of at least three carbon atoms (i.e., propane, butane, pentane, and the like). Since the branched polymers of the invention combine at least two polymer arms in a single molecule, a polymer with sufficient molecular weight to impart beneficial properties to a biologically active molecule, such as increased water solubility, can be formed using shorter, easier to prepare polymer chains. The branched polymers of the invention are preferably monofunctional, meaning the polymer molecule contains only a single reactive site for conjugation to a biologically active molecule. Use of a monofunctional polymer eliminates the possibility of crosslinking with a biologically active molecule, such as a protein, which can lead to loss of activity.

As described in greater detail below, for branched polymers of the invention comprising poly(alkylene glycol) polymer arms, such as PEG arms, the branched polymers are advantageously synthesized by polymerizing alkylene oxide monomer units, such as ethylene oxide units, directly onto an aliphatic hydrocarbon core molecule substituted with two or more nucleophilic groups (e.g., thiol, amino or hydroxyl groups). In this manner, expensive and time-consuming polymer purification steps associated with prior art methods are avoided.

Typically, the total number average molecular weight of the branched reactive polymers of the invention will be about 500 to about 100,000 daltons (Da), preferably about 5,000 to about 60,000 Da, most preferably about 8,000 to about 40,000 Da. Each polymer arm of the branched polymer will typically have a molecular weight of about 250 Da to about 50,000 Da, more preferably about 2,500 to about 30,000 Da, and most preferably about 4,000 to about 20,000 Da. Branched polymers having a total number average molecular weight of about 500 Da, about 1,000 Da, about 2,000 Da, about 4,000 Da, about 5,000 Da, about 8,000 Da, about 10,000 Da, about 12,000 Da, about 15,000 Da, about 20,000, about 25,000 Da, and about 30,000 Da are particularly preferred.

A branched reactive polymer of the invention will typically comprise at least two water-soluble and non-peptidic polymer arms, such as poly(ethylene glycol) arms, covalently attached to an aliphatic hydrocarbon core structure bearing a single functional group. A generalized structure of the branched reactive polymers of the invention is shown below:

$$Y-(X)p-R(-X'-POLY)_q \qquad \text{Formula I}$$

wherein:

R is an aliphatic hydrocarbon having a length of at least three carbon atoms;

each POLY is a water soluble and non-peptidic polymer, such as PEG;

X' is a heteroatom linkage, preferably —NH—, —O—, or —S—;

X is a linker;

p is 0 or 1;

q is 2 to about 10, preferably 2 to about 5 (e.g., 2, 3, 4, or 5); and

Y is a functional group.

The aliphatic hydrocarbon core, R, preferably comprises 3 to about 12 carbon atoms, more preferably 3 to about 7 carbon atoms, most preferably 3 to about 5 carbon atoms. Core structures of 3, 4, and 5 carbon atoms in length are particularly preferred. The aliphatic hydrocarbon can be linear or branched and may include one or more heteroatoms in the hydrocarbon chain. In a preferred embodiment, the polymer arms, POLY, and the functional group, Y, are each attached to different carbon atoms of the core molecule. For example, in a three-carbon core embodiment, the POLY polymer arms are preferably attached at the 1- and 3-position and the Y functional group is preferably attached at the 2-position.

The branched polymers of the invention are preferably symmetrical, meaning the polymer arms are symmetrically located on the central core, R (e.g., at the 1- and 3-position of a three-carbon aliphatic core). A symmetrical arrangement lends itself to the preferential formation of only one polymer product having polymer arms of approximately the same number of subunits, since the initiation of the polymerization process should occur at approximately equal rates in equivalent arm positions extending from a symmetrical core.

A. Polymer Arms

In general, the water soluble and non-peptidic polymer portion of the branched polymer structure (i.e., POLY in Formula I above) should be non-toxic and biocompatible, meaning that the polymer is capable of coexistence with living tissues or organisms without causing harm. When referring to a branched reactive polymer, it is to be understood that the polymer can be any of a number of water soluble and non-peptidic polymers, such as those described herein as suitable for use in the present invention. Preferably, POLY as designated in Formula I above is poly(ethylene glycol) (PEG). The term PEG includes poly(ethylene glycol) in any of a number of geometries or forms, including linear forms (e.g., alkoxy PEG or bifunctional PEG), branched or multi-arm forms (e.g., forked PEG or PEG attached to a polyol core), pendant PEG, or PEG with degradable linkages therein, to be more fully described below. Preferred for forming the branched polymers of the invention are linear polymers such as linear forms of PEG.

In its simplest form, PEG has the formula $$-CH_2CH_2O-(CH_2CH_2O)_n-CH_2CH_2- \qquad \text{Formula II}$$

wherein n is from about 5 to about 1,200, typically from about 50 to about 700.

End-capped polymers, meaning polymers having at least one terminus capped with a relatively inert group (e.g., an alkoxy group), can be used as a polymer of the invention. For example, methoxy-PEG-OH, or mPEG in brief, is a form of PEG wherein one terminus of the polymer is a methoxy group, while the other terminus is a hydroxyl group that is subject to ready chemical modification. The structure of MPEG is given below.

$$CH_3O-(CH_2CH_2O)_n-CH_2CH_2-OH \qquad \text{Formula III}$$

wherein n is as described above.

Multi-armed or branched PEG molecules, such as those described in U.S. Pat. No. 5,932,462, which is incorporated by reference herein in its entirety, although less preferred, can also be used as the PEG polymer in the branched reactive polymers of the invention. For example, an exemplary branched PEG polymer can have the structure:

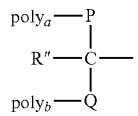

Formula IV wherein:

$poly_a$ and $poly_b$ are PEG backbones, such as methoxy poly (ethylene glycol);

R" is a nonreactive moiety, such as H, methyl or a PEG backbone; and

P and Q are nonreactive linkages. In a preferred embodiment, the branched PEG polymer is methoxy poly(ethylene glycol) disubstituted lysine. As would be appreciated by one of skill in the art, use of branched polymers as the POLY polymer arms in the branched reactive polymers of the invention would result in a polymer having multiple branching points within the molecule. Such polymers, if utilized to prepare the branched structures of the invention, are attached to the aliphatic core structures provided herein not by polymerization but by covalent attachment.

Although less preferred due to its multifunctional nature, the PEG polymer may alternatively comprise a forked PEG. Generally speaking, a polymer having a forked structure is characterized as having a polymer chain attached to two or more active agents via covalent linkages extending from a hydrolytically stable branch point in the polymer. An example of a forked PEG is represented by -PEG-YCHZ$_2$, where Y is a linking group and each Z is an activated terminal group for covalent attachment to a biologically active agent. The Z group is linked to CH by a chain of atoms of defined length. International Application No. PCT/US99/05333, the contents of which are incorporated by reference herein, discloses various forked PEG structures capable of use in the present invention. The chain of atoms linking the Z functional groups to the branching carbon atom serve as a tethering group and may comprise, for example, an alkyl chain, ether linkage, ester linkage, amide linkage, or combinations thereof. In this embodiment of the invention, the resulting branched polymer is multifunctional, i.e., having reactive sites suitable for attachment to a biologically active molecule not only extending from the aliphatic core, but also extending from the forked polymer arm(s). As in the above case, such forked polymers, if utilized to prepare the branched structures of the invention, are attached to the aliphatic core structures provided herein not by polymerization but typically by covalent attachment.

Again, although less favored due to its multifunctional nature, the PEG polymer may comprise a pendant PEG molecule having reactive groups, such as carboxyl, covalently attached along the length of the PEG backbone rather than at the end of the PEG chain. The pendant reactive groups can be attached to the PEG backbone directly or through a linking moiety, such as an alkylene group.

In addition to the above-described forms of PEG, the polymer arms (POLY) can also be prepared with one or more weak or degradable linkages in the polymer backbone, including any of the above described polymers. For example, PEG can be prepared with ester linkages in the polymer backbone that are subject to hydrolysis. As shown below, this hydrolysis results in cleavage of the polymer into fragments of lower molecular weight:

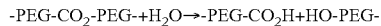

-PEG-CO$_2$-PEG-+H$_2$O→-PEG-CO$_2$H+HO-PEG-

Other hydrolytically degradable linkages, useful as a degradable linkage within a polymer backbone, include carbonate linkages; imine linkages resulting, for example, from reaction of an amine and an aldehyde (see, e.g., Ouchi et al., Polymer Preprints, 38(1):582-3 (1997), which is incorporated herein by reference.); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

In one instance, the polymer arms having one or more hydrolyzable linkages contained therein are prepared in a two-step polymerization process which includes an intermediate step for inclusion of the desired hydrolyzable linkage. That is to say, polymerization of, e.g., ethylene oxide subunits, onto the central core is carried out to a certain desired chain length and the reactive polymer termini extending from the central core are then coupled to short polymer chains suitably functionalized at one end to react with the hydroxyl groups of the intermediate polymer arms extending from the core to introduce the hydrolyzable linkage(s). Further polymerization of ethylene oxide subunits onto the polymer arms, now containing one or more hydrolyzable linkages, is then carried out to prepare polymer arms of a desired chain length.

It is understood by those skilled in the art that the term poly(ethylene glycol) or PEG represents or includes all the above forms of PEG.

Any of a variety of monofunctional, bifunctional or multifunctional polymers that are non-peptidic and water-soluble can also be used to form the branched polymers in accordance with the present invention. The polymer backbone can be linear, or can be in any of the above-described forms (e.g., branched, forked, and the like). Examples of suitable polymers include, but are not limited to, other poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(acrylic acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof.

Typically, the two or more polymer arms of a branched polymer of the invention are the same. That is to say, most preferably, the polymer arms are each a poly(ethylene glycol) or each a polyolefinic alcohol, etc. Generally, not only are the polymer arms composed of the same type of subunits, but they also have identical geometries and similar molecular weights. That is to say, in a most preferred embodiment of the invention, the polymer arms extending from the aliphatic core are identical.

B. Linker (X)

The branched polymers of the invention optionally include a linkage (i.e., X in Formula I) that joins a branching carbon of the aliphatic hydrocarbon central core molecule with the functional group, Y. The structure of the X linkage is typically determined by the structure of the aliphatic hydrocarbon core used to form the polymers of the invention and has an overall length of from 1 to about 40 atoms, preferably 1 to about 10 atoms, and most preferably 1 to about 5 atoms. Preferred linkages include heteroatoms such as —O— or —S—, -alkylene-, —O-alkylene-O—, -alkylene-O-alkylene-, -aryl-O— (e.g., -phenylene-O—), —O-aryl- (e.g., —O-phenylene), (—O-alkylene-)$_m$, and (-alkylene-O—)$_m$, wherein m is 1-10, preferably 1-5 (e.g., 1, 2, 3, 4, or 5). The alkylene groups of the X linkage are preferably C1-C6alkylene, more preferably C1-C3alkylene, including methylene and ethylene.

In some instances, it may be advantageous to have a linker (i.e., X in Formula I) extending the point of covalent attachment of the biologically active agent away from the central aliphatic core. In such particular embodiments of the invention, the terminus for activation and subsequent attachment to an active agent is then at a primary rather than at a secondary carbon position, thereby increasing the ease of subsequent modifications due to the increased reactivity of a primary carbon in nucleophilic displacement reactions.

C. Functional Group (Y)

The Y functional group can be any functional group suitable for reaction with a functional group on a biologically active molecule or a functional group that is a precursor thereof. Examples of suitable functional groups include hydroxyl, active ester (e.g., N-hydroxysuccinimidyl ester and 1-benzotriazolyl ester), active carbonate (e.g., N-hydroxysuccinimidyl carbonate, 1-benzotriazolyl carbonate, p-nitrophenyl carbonate), acetal, aldehyde having a carbon length of 1 to 25 carbons (e.g., acetaldehyde, propionaldehyde, and butyraldehyde), aldehyde hydrate, alkenyl, acrylate, methacrylate, acrylamide, active sulfone, amine, hydrazide, thiol, alkanoic acids having a carbon length (including the carbonyl carbon) of 1 to about 25 carbon atoms (e.g., carboxylic acid, carboxymethyl, propanoic acid, and butanoic acid), acid halide, isocyanate, isothiocyanate, maleimide, vinylsulfone, dithiopyridine, vinylpyridine, iodoacetamide, epoxide, glyoxal, dione, mesylate, tosylate, and tresylate.

Exemplary functional groups are also described in the following references, all of which are incorporated by reference herein: N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al., Makromol. Chem. 180:1381 (1979), succinimidyl ester (see, e.g., U.S. Pat. No. 4,670, 417), benzotriazole carbonate (see, e.g., U.S. Pat. No. 5,650, 234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Bio/Technology 8:343 (1990), Romani et al. in Chemistry of Peptides and Proteins 2.29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900,461).

In one embodiment of the invention, the Y functional group is a protected functional group, such as a protected hydroxyl group of formula —O-Gp, wherein Gp is a protecting group. The Gp protecting group can be any of various hydroxyl protecting groups known in the art, such as benzyl or other alkylaryl groups (e.g., groups having the formula —CH$_2$—Ar, wherein Ar is any aryl group), acetal, and dihydropyranyl. Other suitable protecting groups are described in Greene, T. W., et al., *PROTECTIVE GROUPS IN ORGANIC SYNTHESIS,* 3rd ed., John Wiley & Sons, New York, N.Y. (1999). As would be readily understood, the protecting group, Gp, can be readily displaced from the molecule to form a hydroxyl group, which can be further modified to form other functional groups using techniques known in the art.

D. Core Structures

The branched polymers of the invention are composed of an aliphatic hydrocarbon-based core (i.e., R in Formula I above) having a length of least three carbon atoms, preferably from 3 to 7 carbon atoms. That is to say, a central core structure will typically contain at its core a number of carbon atoms selected from the following: 3, 4, 5, 6, 7 or more carbon atoms. Preferred are core structures containing 3, 5 or 7 core carbons. Although the carbon atoms of the central core may have polymer arms extending from any of the aforementioned carbons, preferably but not necessarily, the overall branched polymer is symmetrical. That is to say, for a three-carbon core, the polymer arms preferably extend from positions 1 and 3, with a site suitable for covalent attachment to a biologically active molecule extending from the central carbon or the carbon at position 2. Similarly, for a five carbon core, the polymer arms extend from positions 1 and 5, with a site suitable for covalent attachment to a biologically active molecule extending from position 3, or polymer arms extending from positions 2 and 4, or, if a highly branched structure is desired, with polymer arms extending from each of positions 1, 2, 4, and 5. Exemplary three-carbon core structures possessing as the nucleophile an oxygen atom directly attached to carbons 1 and 3 are provided in the Examples. These examples demonstrate synthetic approaches for building core structures having a variety of (X)p groups. Preferably, the nucleophiles (heteroatoms) attached to the central core are the same, e.g., all oxygen, all nitrogen, etc.

Although less preferred, suitable for use in forming the branched polymers of the invention are unsymmetrical core structures such as those derived from 2-aminopentanedioic acid (glutamic acid), 2-aminosuccinic acid (aspartic acid), and the like. In utilizing core structures such as these, the terminal acid groups are typically activated for coupling with a reactive polymer to form the branched polymer core. Alternatively, the carboxylic acid groups are reduced with a reducing agent to form the corresponding diol, which then possesses sites suitable for building the polymer chains, for example, by a catalyzed reaction of the N-protected diol with an appropriate monomer subunit and subsequent polymerization thereof directly onto the central core.

E. Exemplary Branched Reactive Polymer Structures

More specific structural embodiments of the branched polymers of the invention will now be described, all of which are intended to be encompassed by the structure of Formula I above. The specific structures shown below are presented as exemplary structures only, and are not intended to limit the scope of the invention.

One embodiment of the invention having a three-carbon core has the structure:

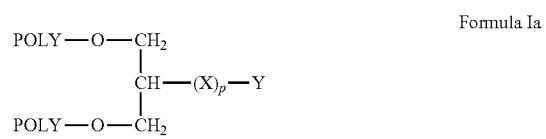

Formula Ia wherein POLY, X, p, and Y are described above.

In a preferred embodiment of Formula Ia, the branched polymer of the invention has the structure:

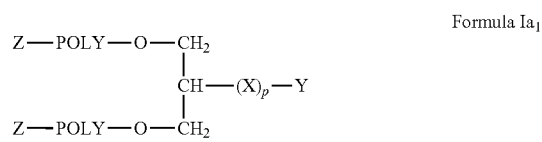

Formula Ia$_1$ wherein:

Z is a capping group or a functional group; and

POLY, X, p, and Y are described above.

The Z group is preferably a relatively inert capping group, such as alkoxy (e.g. methoxy or ethoxy), alkyl, benzyl, aryl, or aryloxy (e.g. benzyloxy). Alternatively, the Z group is a functional group capable of readily reacting with a functional group on a biologically active molecule, such as any of the functional groups discussed above for the Y functional group.

In another embodiment of Formula Ia, each POLY is PEG end-capped with methoxy as shown below:

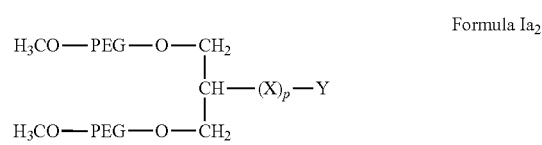

Formula Ia$_2$

In yet another embodiment of Formula Ia, the X linkage is absent as shown below:

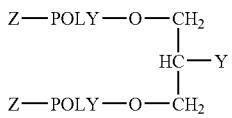

Formula Ia$_3$ wherein:

Z, POLY, and Y are defined above. Preferably, Z is methoxy and POLY is PEG.

In a further embodiment of Formula Ia, the X linkage is one of the specific linkages shown below:

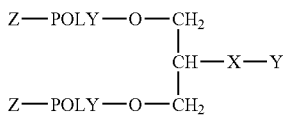

Formula Ia$_4$ wherein:

X is —CH$_2$CH$_2$—O—CH$_2$CH$_2$— or —O—CH$_2$CH$_2$—; and

Z, POLY and Y are defined above. Preferably, Z is methoxy and POLY is PEG.

As described above, other heteroatoms, such as —NH— or —S— could be used in place of the —O-linkages illustrated in Formulas Ia, Ia$_1$, Ia$_2$, Ia$_3$, and Ia$_4$ above.

F. Method of Forming Branched Reactive Polymers

The branched polymers of the invention are formed by attaching polymer arms to a heteroatom-substituted aliphatic hydrocarbon core molecule having at least three carbon atoms, such as propane, via heteroatom linkages (e.g., —NH—, —O— or —S—). Although the polymer arms may be attached to the aliphatic hydrocarbon structure by simply reacting terminal functional groups on preformed purified polymers with reactive nucleophiles on the aliphatic hydrocarbon core without departing from the invention, for poly(alkylene glycol) polymers, it is preferable in many respects to directly polymerize alkylene oxide monomer units, such as ethylene oxide, propylene oxide, or butylene oxide subunits, onto an aliphatic hydrocarbon core bearing at least two available hydroxyl groups (or other nucleophilic groups such as amino or thiol groups). As illustrated in the Examples, alkylene oxide units can be polymerized onto, for example, an alcohol molecule using a catalyzed reaction to form ether-linked polymer arms, preferably using base catalysis although other catalysts such as metal or acid catalysts could also be employed. By polymerizing the alkylene oxide directly onto a suitably functionalized aliphatic hydrocarbon core structure, the branched polymer can be formed without first forming and purifying high molecular weight polymers, which is technically challenging, expensive, and time-consuming.

The aliphatic hydrocarbon core molecule comprises two or more available nucleophilic groups, such as hydroxyl groups, depending on the number of polymer arms to be attached to the core molecule. In one particular embodiment, the aliphatic hydrocarbon has two hydroxyl groups. The core molecule also bears at least one protected functional group, such as a protected hydroxyl group (i.e., —O-Gp, where Gp is described above). Preferably, the aliphatic hydrocarbon is 1,3-dihydroxy-2-substituted propane, wherein the protected hydroxyl group is attached at the 2-position, optionally via an intervening linkage (i.e., X in Formula I above). The presence of the protecting group prevents polymerization at that position, thereby ensuring that at least one side chain of the aliphatic hydrocarbon core will be available for further modification, for example, to a form suitable for covalent attachment to a biologically active molecule.

The generalized structure for the aliphatic hydrocarbon core molecule of the invention is shown below:

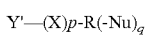

Formula V wherein:

Y' is a protected functional group, such as a protected hydroxyl group, wherein the presence of the protecting group prevents polymerization at the Y' position on the aliphatic core, R;

Nu is a nucleophile, such as amino, thiol or hydroxyl; and

R, X, p and q are defined above.

Unlike certain prior art applications that utilize a polyol or polyamine core molecule to form a highly cross-linked hydrogel, the present invention utilizes a nucleophile-substituted aliphatic hydrocarbon core molecule to form a branched polymer suitable for covalent coupling to a biologically active molecule.

The generalized structure for a preferred hydroxyl-substituted three-carbon aliphatic hydrocarbon core structure is shown below:

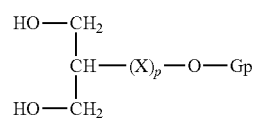

Formula Va wherein:

X, p, and Gp are defined above.

Exemplary core structures of Formula Va include 2-benzyloxy-1,3-propanediol, 2-benzyloxyethoxy-1,3-propanediol, and 2-benzyloxyethoxyethyl-1,3-propanediol. The core structures of Formula V are either commercially available (See Examples 1-2) or can be prepared from commercially available reagents (See Examples 3-4).

Base-initiated polymerization of ethylene oxide onto a hydroxyl-substituted aliphatic hydrocarbon of Formula Va results in a branched polymer of Formula Ia where Y is —O-Gp and POLY is -PEG-OH. Thereafter, in order to form a monofunctional branched polymer, the terminal hydroxyl groups of the PEG polymer chains are preferably alkylated (e.g., methylated to form MPEG) by reaction with an alkylating agent, such as methyl toluenesulfonate.

Following alkylation of the terminus of the PEG chains, the protecting group, Gp, can be displaced by hydrolysis or hydrogenolysis to produce a hydroxyl group. As would be understood, the hydroxyl group can then be modified or converted to other reactive groups as desired, such as the reactive groups listed above for the Y moiety of Formula I.

III. BIOLOGICALLY ACTIVE CONJUGATES OF BRANCHED REACTIVE POLYMERS

The present invention also includes biologically active conjugates comprising a biologically active molecule covalently attached to a branched polymer of the invention. As noted above, the branched polymers of the invention are preferably although not necessarily monofunctional (e.g., they may also be bifunctional or less preferably multifunctional), and the biologically active agent is preferably attached to the branched polymer via a linkage formed from reaction of the functional group on the branched polymer and a functional group on the biologically active agent.

The specific linkage will depend on the structure of the functional groups utilized, and will typically be governed by the functional groups contained in the biologically active molecule. For example, an amide linkage can be formed by reaction of a branched polymer bearing a carboxylic acid group, or an active ester thereof, in the presence of a coupling agent, such as DCC, DMAP, or HOBT, with a biologically active agent having an amine group. Alternatively, a sulfide linkage can be formed by reaction of a branched polymer bearing a thiol group with a biologically active agent bearing a hydroxyl group. In another embodiment, an amine linkage is formed by reaction of a branched polymer bearing an amino group with a biologically active molecule bearing a hydroxyl group. In yet another embodiment, a branched polymer bearing a carboxylic acid is reacted with a biologically active molecule bearing a hydroxyl group in the presence of a coupling agent to form an ester linkage. The particular coupling chemistry employed will depend upon the structure of the biologically active agent, the potential presence of multiple functional groups within the biologically active molecule, the need for protection/deprotection steps, chemical stability of the molecule, and the like, and will be readily determined by one skilled in the art. Illustrative linking chemistry useful for preparing the branched polymer conjugates of the invention can be found, for example, in Wong, S. H., (1991), "*Chemistry of Protein Conjugation and Crosslinking*", CRC Press, Boca Raton, Fla. and in Brinkley, M. (1992) "*A Brief Survey of Methods for Preparing Protein Conjugates with Dyes, Haptens, and Crosslinking Reagents*", in *Bioconjug. Chem.*, 3, 2013.

The linkage (i.e., $L_1$ in Formula VI below) can be hydrolytically degradable so that the biologically active agent is released into circulation over time after administration to a patient. Exemplary hydrolytically degradable linkages include carboxylate ester, phosphate ester, anhydrides, acetals, ketals, acyloxyalkyl ether, imines, orthoesters, peptides and oligonucleotides. If desired, a hydrolytically stable linkage, such as amide, urethane (also known as carbamate), amine, thioether (also known as sulfide), and urea (also known as carbamide) linkages, can also be used without departing from the invention.

A generalized structure for a biologically active conjugate of the invention comprising a branched polymer of Formula I can be represented as shown below:

$$D\text{-}L_1\text{-}(X)p\text{-}R(\!-\!X'\text{-}POLY)_q \qquad \text{Formula VI}$$

wherein:

D is a biologically active molecule, such as a peptide, protein, enzyme, small molecule drug, dye, lipid, nucleoside, nucleotide, oligonucleotide, polynucleotide, nucleic acid, polysaccharide, steroid, cell, virus, liposome, microparticle, micelle, fat, electrolyte and the like;

$L_1$ is a linkage resulting from the reaction of the functional group of the branched polymer (i.e., Y in Formula I) and a functional group on the biologically active molecule; and POLY, X, X', q and p are defined above.

In one preferred embodiment, the biologically active conjugate has the structure:

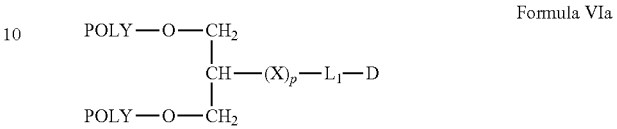

Formula VIa wherein:

D, $L_1$, POLY, X, and p are defined above.

A biologically active agent for use in coupling to a branched polymer of the invention may be any one or more of the following. Suitable agents may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

Examples of active agents suitable for use in covalent attachment to a branched polymer of the invention include, but are not limited to, calcitonin, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX insulin, pro-insulin, insulin analogues (e.g., monoacylated insulin as described in U.S. Pat. No. 5,922,675), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, flerofloxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, cefibuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

IV. EXAMPLES

The following examples are given to illustrate the invention, but should not be considered in limitation of the invention. For example, although PEG is used in the examples to illustrate the invention, other polymers that are useful in the practice of the invention are encompassed by the invention as discussed above.

All PEG reagents referred to in the appended examples are available from Shearwater Corporation of Huntsville, Ala. All other reagents are commercially available. All $^1$HNMR data was generated by a 300 or 400 MHz NMR spectrometer manufactured by Bruker.

Examples 1-2 illustrate a method of forming a branched reactive polymer of the invention using a commercially available hydroxyl-substituted aliphatic hydrocarbon core molecule (2-benzyloxy-1,3-propanediol). In Example 1, the branched polymer is functionalized with an acetaldehyde diethyl acetal. In Example 2, the branched polymer is functionalized with a succinimidyl ester of butyric acid. Examples 3-4 illustrate a method of synthesizing two additional core molecules having intervening linkages between the aliphatic hydrocarbon core molecule and the protected hydroxyl side chain. Examples 5-6 illustrate PEGylation of an enzyme with a branched polymer of the invention to form a conjugate.

Example 1

Synthesis of 2-(1,3-di-mPEGoxy-2-propanoxy) acetaldehyde diethyl acetal

A. Synthesis of 1,3-diPEGoxy-2-benzyloxypropane [MW poly(ethylene glycol) (PEG)=9 kda]]

A 500 ml round bottom flask was charged with 250 ml of freshly distilled, dry THF containing 2-benzyloxy-1,3-propanediol (0.84 g, 4.59 mmole). Potassium naphthalenide was added (0.28 M, 16.4 ml) with continuous stirring under an inert atmosphere. The flask was then cooled to 0° C. in an ice bath. Ethylene oxide (50.0 ml, 1.02 moles) was added via a cooled syringe. The reaction was allowed to warm to room temperature and was stirred for 72 hours. The reaction was quenched by the addition of 5 ml of 0.2M acetic acid. The solvents were removed by rotary evaporation and the crude material redissolved in 100 ml of methylene chloride. The product was precipitated by the addition of 400 ml of diethyl ether and collected by filtration. The product was dried under vacuum.

Yield: 42 g. (93%). $^1$H nmr (400 MHz DMSO-$d_6$), δ7.25-7.34, (m, 5H), 4.6 (s, 2H), 3.2-3.8 (m, 826H).

B. Methylation of 1,3-diPEGoxy-2-benzyloxypropane 1,3-diPEGoxy-2-benzyloxypropane [MW poly(ethylene glycol) (PEG)=9 kDa] (5.0 g, 0.55 mmoles) from Step A was placed in a two-necked round bottom flask and dissolved in 150 ml of toluene. The flask was fitted with a septum and a Dean-Stark trap and the compound was azeotropically dried under an inert atmosphere. The trap was replaced with a reflux condenser and the temperature of the flask was kept at 45° C. by placing the flask in a constant temperature oil bath. Methyl toluenesulfonate (1.62 ml, 5.4 mmoles) and 2.8 ml of potassium t-butoxide solution (1.0 M in THF) was added and the reaction stirred for 3 hours. Methyl toluenesulfonate (0.81 ml) and 1.4 ml of potassium t-butoxide solution were then added and the reaction was stirred for an additional 3 hours. The flask was removed from the oil bath and cooled to room temperature. The solution was transferred to a single-necked round bottom flask and the solvent was removed by rotary evaporation. The residue was dissolved in 5 ml of methylene chloride and precipitated by the addition of 50 ml of diethyl ether. The product was collected by filtration and dried under vacuum.

Yield: 4.2 g. $^1$H Nmr (400 MHz DMSO-$d_6$), δ 7.25-7.34 (m, 5H) 4.6 (s, 2H), 3.3-3.8 (m, 826H), 3.24 (s, 6H).

C. Debenzylation of 1,3-di-mPEGoxy-2-benzyloxypropane 1,3-di-mPEGoxy-2-benzyloxypropane [MW poly(ethylene glycol) (PEG)=9 kDa] (2.9 g, 0.32 mmoles) from Step B was dissolved in 100 ml ethanol. Pd(OH)$_2$/C (0.5 g) and cyclohexene (10 ml) was added and the mixture was refluxed for 4 hours. After cooling to room temperature, the mixture was filtered and the filtrate solvent removed by rotary evaporation. The crude residual material was dissolved in 5 ml of methylene chloride and precipitated by the addition of 50 ml of diethyl ether. The product was collected by filtration and dried under vacuum.

$^1$H Nmr (300 MHz, DMSO-d$_6$), δ 4.76 (d, 1H), 3.3-3.8 (m, 826H), 3.24 (s, 6H).

D. Synthesis of 2-(1,3-di-mPEGoxy-2-propanoxy) acetaldehyde diethyl acetal

To 2-hydroxy-1,3-di-mPEGoxypropane from Step C (M.W. 9000 Da, 4.5 g, 0.0005 moles) in dioxane (250 ml) is added sodium hydroxide (0.20 g, 0.005 moles) and chloroacetaldehyde diethyl acetal (0.38 g, 0.0025 moles) and the mixture is refluxed 24 h with vigorous stirring. The solution is concentrated to about 150 ml, cooled, and filtered. The filtrate is evaporated to dryness, dissolved in 100 ml of water, and extracted with methylene chloride (3×75 ml). The combined extracts are dried over sodium sulfate, concentrated, and the product precipitated by addition of 300 ml of ether. The precipitated product is collected by filtration and dried under vacuum.

This reaction demonstrates conversion of the 2-benzyloxypropane protecting group to a protected form of an aldehyde (acetaldehyde diethyl acetal) suitable for covalent coupling with amino groups on a protein or other biologically active agent.

Example 2

Synthesis of 2-(1,3-di-mPEGoxy-2-propanoxy) succinimidyl butyrate (mPEG2-SBA) (20 kDa)

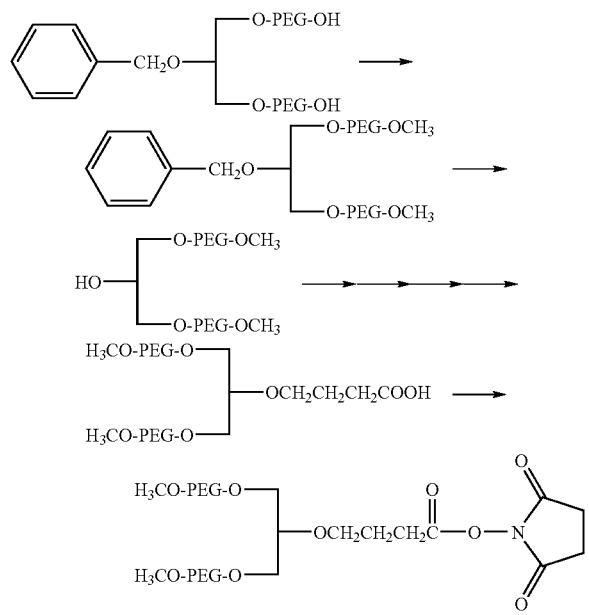

A. Methylation of 1,3-diPEGoxy-2-benzyloxypropane 20 g of 1,3-diPEGoxy-2-benzyloxypropane (20 kDa) prepared as described in Step A of Example 1 and 0.01 g of BHT (2,6-Di-tert-butyl-4-methylphenol) were dissolved in 400 ml of toluene. The resulting solution was azeotropically dried by distillation under reduced pressure. The residue was redissolved in 700 mL of anhydrous toluene and 14 mL of potassium tert-butoxide solution (1.0 M solution in tert-butanol) and 3.0 ml of methyl-toluene sulfonate were added separately. The reaction mixture was stirred overnight at 45° C. under nitrogen.

The insoluble material was filtered and filtrate was evaporated to dryness under reduced pressure. The residue was dissolved in 700 ml of deionized water and saturated with NaCl. The pH of the solution was adjusted to 7.5 and it was then extracted with dichloromethane (300 ml×2). The extracted dichloromethane was dried over Na$_2$SO$_4$, filtered, evaporated and precipitated with Et$_2$O (500 mL). The methylated product was collected by vacuum filtration and dried under vacuum overnight.

Yield: 18.5 g $^1$H nmr (DMSO-d6): δ 7.33 ppm (mult. —OCH$_2$C$_6$H$_5$), δ 4.61 ppm (s. —OCH$_2$C$_6$H$_5$), δ 4.31 ppm (t, —OCH$_2$CH$_2$OMs), 3.5 ppm (br. mult., PEG), δ 3.24 ppm (s, CH$_3$OPEG-).

B. Debenzylation of 1,3-di-mPEGoxy-2-benzyloxypropane 18.0 g of 1,3-di-mPEGoxy-2-benzyloxypropane (20 kDa) from Step A was dissolved in 225 ml of 5 mM phosphate buffer (pH 7.2) and 1.13 g of 10% Pd on charcoal was added. The suspension was hydrogenated 20 hours under 40 psi of hydrogen.

The suspension was filtered to remove catalyst and the filtrate was saturated with NaCl and the pH of the solution was adjusted to 3.0. The solution was extracted with dichloromethane (300 ml×2) and the combined extracts were dried over Na$_2$SO$_4$, filtered, evaporated and precipitated with Et$_2$O (500 mL). The product was collected by vacuum filtration and dried in vacuum overnight.

Yield: 13.2 g; $^1$H nmr (DMSO-d6): δ 4.76 ppm (d. HO—CH—); δ3.5ppm (br. mult., PEG), δ 3.24 ppm (s, CH$_3$OPEG-).

C. Synthesis of 2-(1,3-di-mPEGoxy-2-propanoxy) butyric acid 2.5 g of 2-hydroxy-1,3-di-mPEGoxypropane (20 kDa) from Step B was dissolved in 30 ml of toluene and the resulting solution was azeotropically dried by distillation under reduced pressure. The residue was redissolved in 30 mL of anhydrous toluene and 1 mL of potassium tert-butoxide solution (1.0 M solution in tert-butanol), 2.5 mg of BHT, and 0.25 g of 1-(3-bromopropyl)-4-methyl-2,6,7-trioxabicyclo[2,2,2,] octane were added. The reaction mixture was stirred overnight at 65° C. under nitrogen.

The solvent was evaporated to dryness under reduced pressure, the residue dried under vacuum for 2 hours, and finally redissolved in 60 ml of deionized water. The pH of the solution was adjusted to 2.0 with 10% H$_3$PO$_4$. After stirring at pH 2.0 for 15 min., the pH of the solution was adjusted to 12.0 with 1.0 N NaOH and stirred at pH 12.0 for 2 hours. The hydrolyzed solution was saturated with NaCl and the pH adjusted to 3.0 with 10% H$_3$PO$_4$. The solution was extracted with dichloromethane (100 ml×2) and the combined extracts were dried over Na$_2$SO$_4$, filtered, evaporated and precipitated with Et$_2$O (100 mL). The product was collected by vacuum filtration and dried in vacuum overnight.

Yield: 2.3 g GPC: 79%.

D. Purification of 2-(1,3-di-mPEGoxy-2-propanoxy) butyric acid

The crude 2-(1,3-di-mPEGoxy-2-propanoxy) butyric acid from Step C was purified by DEAE sepharose FF ion exchange column (100 mL). After purification, the yield was 1.55 g.

$^1$H nmr (DMSO-d6): δ3.5 ppm (br. mult., PEG), δ 3.24 ppm (s, C$\underline{H}_3$OPEG-), δ 2.23 ppm (t, —OCH$_2$CH$_2$C$\underline{H}_2$COOH), δ 1.70 ppm (mult. —OCH$_2$C$\underline{H}_2$CH$_2$COOH).

E. Synthesis of 2-(1,3-di-mPEGoxy-2-propanoxy) succinimidyl butyrate (20 kDa)

1.5 g 2-(1,3-di-mPEGoxy-2-propanoxy) butyric acid from Step D was dissolved in 20 ml of anhydrous dichloromethane under nitrogen. N-hydroxysuccinimide (0.0132 g) was first added to the solution followed by 0.0234 g of dicyclohexylcarbodiimide. The solution was stirred overnight at room temperature under nitrogen. The product was filtered, concentrated under vacuum, precipitated into a mixture of IPA and Et$_2$O (1:1), collected by filtration and dried under vacuum.

Yield: 1.2 g; $^1$H nmr (DMSO-d6): δ3.5 ppm (br. mult., PEG), δ 3.24 ppm (s, C$\underline{H}_3$OPEG-), δ 2.80 ppm (s, —NHS), δ 2.70 ppm (t. —OCH$_2$CH$_2$C$\underline{H}_2$COONHS), δ 1.81 ppm (mult. —OCH$_2$C$\underline{H}_2$CH$_2$COONHS).

Example 3

Synthesis of (2'-benzyloxyethoxy)ethyl-1,3-propanediol (BEEP)—An Illustrative Aliphatic Hydrocarbon Core Molecule Suitable for Use in Preparing a Branched Polymer

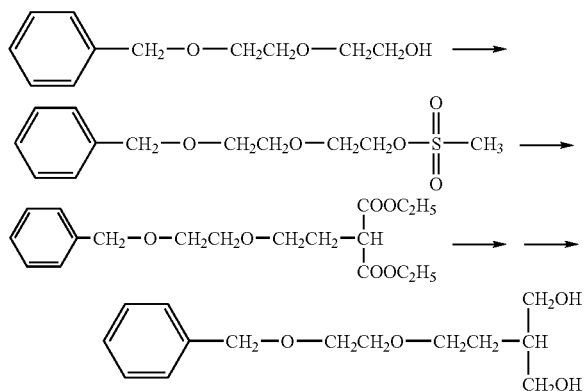

A. Synthesis of di(ethylene glycol) monobenzyl ether methanesulfonate

Di(ethylene glycol) monobenzyl ether (15 g) in 200 ml of toluene was dried by azeotropic distillation and the residue was redissolved in 400 ml of anhydrous toluene and 100 ml of anhydrous dichloromethane. To the solution was added 11.5 ml of dry triethylamine and 6.23 ml of methanesulfonyl chloride dropwise at 0-5° C. The reaction mixture was stirred at room temperature under nitrogen overnight and the reaction was quenched by adding 5 ml absolute ethanol. The insoluble material was filtered off and filtrate was evaporated to dryness. The residue was redissolved in 200 ml of anhydrous toluene and insoluble material was filtered off. The filtrate was evaporated to dryness and residue was dried under vacuum overnight.

Yield: 22 g $^1$H nmr (DMSO-d6): δ 7.33 ppm (mult. —OCH$_2$C$_6$H$_5$), δ 4.49 ppm (s. —OC$\underline{H}_2$C$_6$H$_5$), δ 4.31 ppm (t, OCH$_2$C$\underline{H}_2$OSO$_2$—CH$_3$), δ 3.69 ppm (t, OC$\underline{H}_2$CH$_2$OSO$_2$—CH$_3$), δ 3.59 ppm (mult., —OC$\underline{H}_2$CH$_2$O—), δ 3.24 ppm (s, OCH$_2$CH$_2$OSO$_2$—C$\underline{H}_3$).

B. Synthesis of C$_6$H$_5$—CH$_2$O—CH$_2$CH$_2$OCH$_2$CH$_2$—CH(COOC$_2$H$_5$)$_2$ Diethyl malonate (17.5 g) in 100 ml of 1,4-dioxane was added dropwise NaH (3.6 g) in 150 ml of 1,4-dioxane under nitrogen. Di(ethylene glycol) monobenzyl ether methanesulfonate (10 g) from Step A in 600 ml of 1,4-dioxane was added to the above diethyl malonate solution. After refluxing the mixture for 4 hours, the reaction solution was filtered and evaporated to dryness. The residue was dried in vacuum overnight.

The remaining diethyl malonate was distilled off under reduced pressure. After distillation, the residue was purified by flash chromatography on a silica gel column eluted with hexane followed by dichloromethane. The combined dichloromethane extracts were evaporated to dryness and the product dried under vacuum overnight.

Yield: 6 g. $^1$H nmr (DMSO-d6): δ 7.33 ppm (mult. —OCH$_2$C$_6$H$_5$), δ 4.48 ppm (s. —OC$\underline{H}_2$C$_6$H$_5$), δ 4.10 ppm (mult. OCH$_2$CH$_3$), δ 3.51 ppm (mult., —OCH$_2$CH$_2$O—CH$_2$CH$_2$—, —C$\underline{H}$(CO$_2$—C$_2$H$_5$)$_2$), δ 2.01 ppm (mult. —OCH$_2$C$\underline{H}_2$—CH(CO$_2$—C$_2$H$_5$)$_2$), δ 1.16 ppm (t, —OCH$_2$C$\underline{H}_3$).

C. Synthesis of C$_6$H$_5$—CH$_2$O—CH$_2$CH$_2$OCH$_2$CH$_2$—CH(CH$_2$OH)$_2$ C$_6$H$_5$—CH$_2$O—CH$_2$CH$_2$OCH$_2$CH$_2$—CH(COOC$_2$H$_5$)$_2$ (5 g) from Step B was dissolved in 200 ml of toluene and 29.5 ml of LiAlH$_4$ (1 M in THF) was added at 0-5° C. After stirring overnight at room temperature, 1 ml of water was added followed by 1.0 ml of 15% NaOH and 3.0 ml of water. The insoluble material was filtered and the filtrate was evaporated to dryness. The product was purified by flash chromatography on a silica gel column eluted with ethyl acetate. Combined fractions were evaporated to dryness. The final product was dried under vacuum overnight.

Yield: 1.5 g $^1$H nmr (CDCl$_3$): δ 7.29 ppm (mult. —OCH$_2$C$_6$H$_5$), δ 4.55 ppm (s. —OC$\underline{H}_2$C$_6$H$_5$), δ 3.61 ppm (mult., C$_6$H$_5$CH$_2$—OCH$_2$CH$_2$O—CH$_2$CH$_2$—, —CH(CH$_2$OH)$_2$), δ 1.81 ppm (mult. —OCH$_2$CH$_2$—C$\underline{H}$(CH$_2$OH)$_2$), δ1.65 ppm (mult. —OCH$_2$C$\underline{H}_2$—CH(CH$_2$OH)$_2$).

Example 4

Synthesis of (2'-benzyloxyethoxy)-1,3-propanediol—An Exemplar Aliphatic Hydrocarbon Core Molecule Useful for Preparing a Branched Polymer

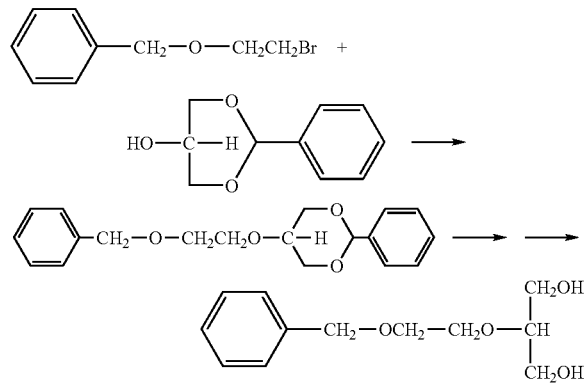

A mixture of 2 g of cis-1,3-O-benzylideneglycerol, 3.51 ml of benzyl 2-bromoethyl ether, 1.25 g of KOH powder and 30 ml of toluene was stirred under reflux for about 20 hours. After cooling to room temperature, the insoluble material was removed by filtration and the filtrate concentrated. The residue was distilled at 140° C. under reduced pressure to remove benzyl 2-bromoethyl ether. After distillation, the residue dissolved in 20 ml of methanol containing 2 ml of conc. HCl and refluxed for 4 hours. 100 ml of water was added and the pH was adjusted to 5-6 with solid NaOH. NaCl was added to ~10% and the product was extracted with dichloromethane (50 ml×3). The combined dichloromethane extracts were dried over $Na_2SO_4$, filtered and evaporated. The residue was dried under vacuum and the product was purified by chromatography on a silica gel column (80 g) eluted with ethyl acetate. The combined fractions were evaporated and dried under vacuum.

Yield: ~0.9 g $^1$H nmr (DMSO-d6): δ 7.31 ppm (mult. —OCH$_2$C$_6$H$_5$), δ 4.48 ppm (s. —OCH$_2$C$_6$H$_5$), δ 4.43 ppm (s. br. —CH(CH$_2$OH)$_2$).), δ 3.67 ppm (t., —OCH$_2$CH$_2$O—CH(CH$_2$OH)$_2$), δ 3.54 ppm (t., —OCH$_2$CH$_2$O—CH(CH$_2$OH)$_2$), δ3.41 ppm (mult. —OCH$_2$CH$_2$O—CH(CH$_2$OH)$_2$), δ3.29 ppm (mult. —OCH$_2$CH$_2$O—CH(CH$_2$OH)$_2$).

Example 5

PEGylation of Lysozyme with a Branched PEG Polymer

Lysozyme (0.0021 g, Sigma)) was dissolved in 1 ml of 50 mM sodium phosphate buffer (pH 7.5) in a 2 ml vial. MPEG2 (20 kDa)-SBA (0.006 g, 2 fold molar excess to the lysozyme) from Example 2 was added and the reaction vial was shaken at room temperature for 18 h.

The MALDI-TOF spectrum of the crude reaction mixture showed lysozyme, PEG2 (20 kDa)-butanoic acid, and mono-, and di-pegylated lysozyme at masses of 14,028 Da, 21,810 Da, 35,612 Da, and 57,783 Da, respectively to be present. SDS-PAGE (10% Tris-HCL gel) displayed six bands indicating tetra-, tri-, di-, mono-pegylated lysozyme (meaning polymer-modified forms of the enzyme having 4, 3, 2, and 1 of the branched polymers of the invention covalently attached thereto, respectively), PEG2 (20K)-butanoic acid, and unpegylated lysozyme.

Example 5 demonstrates the utility of the polymers of the invention in forming conjugates having an amide linkage coupling the branched polymer structure with a biological agent.

Example 6

PEGylation of Lysozyme with Branched PEG Polymer 2.2 mg, 1.9 mg, and 2.1 mg of lysozyme (Sigma) were dissolved in 1 ml of 50 mM sodium phosphate buffer of pH 5.5, 6.5, and 7.6, respectively. 1.5 mg of di-mPEG 2 kDa-butyraldehyde (5 fold molar excess relative to the lysozyme) and 0.1 mg of $NaCNBH_3$ (10 fold molar excess relative to the lysozyme) were added to the lysozyme solution of pH 5.5. 1.3 mg and 1.5 mg of MPEG 2 kDa-butyraldehyde were added to the lysozyme solution of pH 6.5 and 7.5, respectively, followed by the addition of 0.08 mg and 0.09 mg of $NaCNBH_3$, respectively. The three reaction vials were shaken at room temperature for 6 h.

Samples from the reactions of pH 5.5 and 6.5 showed the presence of lysozyme, mono-, and di-pegylated lysozyme by MALDI-TOF. Samples from the reaction conducted at pH 7.5 indicated the presence of only di-pegylated lysozyme by MALDI-TOF. After 24 h all reaction product mixtures contained lysozyme, mono-, and di-pegylated lysozyme, and, tri-pegylated lysozyme.

Three samples withdrawn from the pH 5.5, 6.5, and 7.5 reactions after 6 hours were spotted on a 15% Tris-HCl gel. Each sample showed three visible bands corresponding to di-, mono-, and native lysozyme. Three samples withdrawn from the reactions of pH 5.5, 6.5, and 7.5 after 24 hours showed four visible bands, which indicated tri-, di-, mono-, and unpegylated lysozyme.

Example 6 demonstrates the utility of the polymers of the invention in forming conjugates wherein a biologically active agent is covalently coupled to the branched polymer via a secondary amine linkage generated by reductive amination of the corresponding Schiff base.

What is claimed is:

1. A biologically active conjugate comprising a branched polymer covalently attached to a biologically active molecule, wherein the conjugate has the structure:

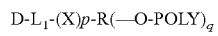

$D-L_1-(X)p-R(—O-POLY)_q$ wherein:
D is the biologically active molecule;
$L_1$ is a linkage resulting from the reaction of a functional group on the linker (X), when present, or on the aliphatic hydrocarbon having a length of at least three carbon atoms (R) of the branched polymer and a functional group of the biologically active molecule;
R is an aliphatic hydrocarbon having a length of at least three carbon atoms;
each POLY is a water soluble and non-peptidic polymer that terminates with a hydroxyl or methoxy group;
X is a linker of 1 to 10 atoms in length;
p is 0 or 1; and
q is 2 to about 10,
and further wherein the branched polymer has a molecular weight of about 12,000 Da to about 100,000 Da.

2. The biologically active conjugate of claim 1, wherein D is selected from the group consisting of peptides, proteins, enzymes, drugs, dyes, lipids, nucleosides, nucleotides, oligonucleotides, polynucleotides, nucleic acids, polysaccharides, steroids, cells, viruses, liposomes, micelles, and fats.

3. The biologically active conjugate of claim 1, having the structure:

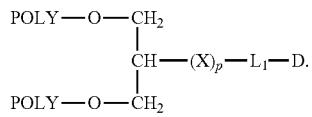

4. The biologically active conjugate of claim 1, wherein the branched polymer has a molecular weight of about 20,000 Da.

5. The biologically active conjugate of claim 1, wherein the branched polymer has a molecular weight of about 40,000 Da.

6. The biologically active conjugate of claim 1, wherein the branched polymer has a molecular weight of about 60,000 Da.

* * * * *